United States Patent
Miyazawa et al.

(10) Patent No.: US 7,750,178 B2
(45) Date of Patent: Jul. 6, 2010

(54) POLYMERIZABLE ACRYLATE COMPOUND CONTAINING HEXAFLUOROCARBINOL GROUP AND POLYMER MADE THEREFROM

(75) Inventors: Satoru Miyazawa, Kawagoe (JP); Satoru Kobayashi, Kawagoe (JP); Takeo Komata, Kawagoe (JP); Kei Matsunaga, Kawagoe (JP)

(73) Assignee: Central Glass Company, Limited, Ube-shi (JP)

( * ) Notice: Subject to any disclaimer, the term of this patent is extended or adjusted under 35 U.S.C. 154(b) by 1106 days.

(21) Appl. No.: 10/563,961

(22) PCT Filed: Feb. 5, 2004

(86) PCT No.: PCT/JP2004/001210

§ 371 (c)(1),
(2), (4) Date: Jan. 10, 2006

(87) PCT Pub. No.: WO2005/005370

PCT Pub. Date: Jan. 20, 2005

(65) Prior Publication Data

US 2006/0217507 A1   Sep. 28, 2006

(30) Foreign Application Priority Data

Jul. 10, 2003   (JP) .............................. 2003-272780

(51) Int. Cl.
*C07C 69/52* (2006.01)
(52) U.S. Cl. ........................ 560/205; 560/219; 560/220; 560/221; 526/242; 526/245; 526/319
(58) Field of Classification Search ................. 560/205, 560/219, 220, 221; 526/245, 242, 319
See application file for complete search history.

(56) References Cited

U.S. PATENT DOCUMENTS

| | | | | |
|---|---|---|---|---|
| 3,438,946 | A | * | 4/1969 | Lichstein et al. ............. 528/299 |
| 4,578,508 | A | * | 3/1986 | Griffith et al. ................ 560/221 |
| 6,784,312 | B2 | * | 8/2004 | Miyazawa et al. ........... 560/205 |
| 7,094,850 | B2 | * | 8/2006 | Miyazawa et al. ........... 526/245 |
| 7,105,618 | B2 | * | 9/2006 | Komoriya et al. ............ 526/242 |
| 7,135,595 | B2 | * | 11/2006 | Allen et al. .................. 560/220 |
| 2003/0078352 | A1 | | 4/2003 | Miyazawa et al. |

FOREIGN PATENT DOCUMENTS

| | | |
|---|---|---|
| EP | 1 341 038 A2 | 9/2003 |
| JP | 60-208311 | 10/1985 |
| WO | WO 02/21213 A2 | 3/2002 |
| WO | WO-2005/005370 A1 * | 1/2005 |

OTHER PUBLICATIONS

T. H. Fedynyshyn, A. Cabral et al., "Fluoroaromatic Resists for 157-nm Lithography", J. Photopolym Sci. Technol., vol. 15, No. 4, (2002) 655-666.
Ralph R. Demmel, Raj Sakamuri et al., "New Resin Systems for 157 nm Lithography", J. Photopolym. Sci. Technol., vol. 14, No. 4, (2001), 603-612.
Loeb, Stephen J., Martin John W.L., et al., Fluorinated alkoxides. Part XII. Studies on potentially tridentate fluorinated diols; zwitterionic and five-coordinate complexes of $Ni^{2+}$ and $CU^{2+}$, Canadian Journal of Chemistry, vol. 56, 2369, (1978).
International Search Report dated Apr. 20, 2004 w/English translation (Three (3) pages).
European Search Report dated Aug. 10, 2006 (three (3) pages).
European Office Action dated Sep. 24, 2009 (Three (3) pages).

* cited by examiner

*Primary Examiner*—Peter D. Mulcahy
*Assistant Examiner*—Henry Hu
(74) *Attorney, Agent, or Firm*—Crowell & Moring LLP

(57) ABSTRACT

The present invention relates to a polymerizable acrylate compound represented by the general formula (1):

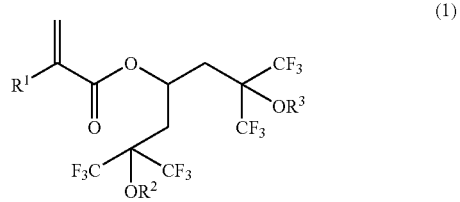

(1)

(in the formula, $R^1$ represents a hydrogen atom, halogen atom, hydrocarbon group or fluorine-containing alkyl group, $R^2$ and $R^3$ may be different or identical, and each of them independently is a hydrogen atom, fluorine atom, hydrocarbon group optionally branched, fluorine-containing alkyl group, aromatic group, or cyclic structure containing an aliphatic group and may contain oxygen or carbonyl bond) and a polymer compound obtained by using the same.

13 Claims, No Drawings

POLYMERIZABLE ACRYLATE COMPOUND CONTAINING HEXAFLUOROCARBINOL GROUP AND POLYMER MADE THEREFROM

BACKGROUND OF THE INVENTION

The present invention relates to novel fluorine-containing polymerizable acrylate compounds containing a specific structure, that is, hexafluorocarbinol group or its protected or modified substituent, and polymers obtained by polymerization or copolymerization using the same.

Fluorine-containing compounds have been used or developed in a wide applied field centered at advanced material fields, due to characteristics, such as water repellency, oil repellency, low water absorption, heat resistance, weather resistance, corrosion resistance, transparency, photosensitivity, low refractive index, and low dielectric property. In particular, in the case of utilizing characteristics of transparency behavior in each wavelength range, there are active researches and developments going on in the coating fields such as anti-reflection films, to which low refractive indexes and visible light transparency have been applied, optical devices, to which transparency in long wavelength band (optical communication wavelength band) has been applied, and resist materials, to which transparency in ultraviolet region (particularly vacuum ultraviolet wavelength region) has been applied. As a common high-molecule design in these applied fields, it is tried to achieve good adhesion to substrate and high glass transition point (Tg), that is, high hardness, while achieving transparency in each wavelength for use by introducing as many fluorine atoms as possible. There are various proposals of increasing transparency at each wavelength by increasing the fluorine content as material design. However, there are few examples on improving fluorine-containing monomers themselves in hydrophilicity and adhesion and on obtaining high Tg. Recently, in next generation $F_2$ resist field of vacuum ultraviolet region, there were reports on a hydroxyl-containing fluorostyrene (see T. H. Fedynyshyn, A. Cabral et al., J. Photopolym. Sci. Technol., 15, 655-666 (2002)) and on a hydroxyl-containing fluoronorbornene compound (see Ralph R. Dammel, Raj Sakamuri et al., J. Photopolym. Sci. Technol., 14, 603-611 (2001)). Thus, there was emerged an idea of containing fluorine and making polarity of hydroxyl group coexistent. However, compatibility between transparency in ultraviolet rays and etching resistance is still insufficient, and there exist many factors to be improved. Thus, these conventional compounds are not necessarily sufficient in capability, and there has been a demand for creating a novel monomer or its raw material capable of efficiently providing further improved high-molecular compounds.

SUMMARY OF THE INVENTION

It is an object of the present invention to provide a fluorine-containing acrylate compound, which is a novel polymerizable monomer, by having high fluorine content and polar group in the same molecule, and a polymer compound using the same.

The present invention provides a polymerizable acrylate compound represented by the general formula (1):

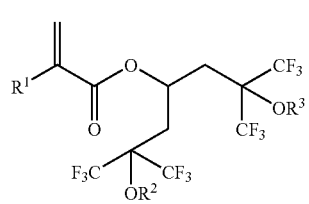

(1)

(in the formula, $R^1$ represents a hydrogen atom, halogen atom, hydrocarbon group or fluorine-containing alkyl group, $R^2$ and $R^3$ may be different or identical, and each of them independently is a hydrogen atom, fluorine atom, hydrocarbon group optionally branched, fluorine-containing alkyl group, aromatic group, or cyclic structure containing an aliphatic group and may contain oxygen or carbonyl bond.) and a polymer compound obtained by polymerization or copolymerization using the same.

DESCRIPTION OF THE PREFERRED EMBODIMENTS

In the present invention, there have been synthesized a series of novel fluorine-containing acrylate compounds as specific compounds containing two hexafluorocarbinol groups in the same molecule and polymer compounds using those monomers, thereby completing the present invention. However, it is possible to protect or modify the hexafluorocarbinol group with a substituent that is described in the after-mentioned $R^2$ and $R^3$.

According to the present invention, there is provided a novel, fluorine-containing, polymerizable, acrylate compound and a polymer compound using the same.

In a specific acrylate represented by the general formula (1) according to the present invention, fluorine and hydroxyl group coexist as a hexafluorocarbinol group in the molecule. Firstly, a monomer of the general formula (1) usable in the present invention is described.

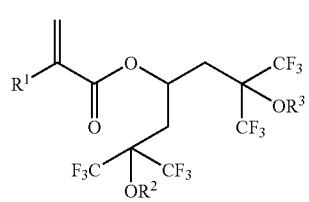

(1)

$R^1$ usable in the general formula (1) of the present invention can be used without particular limitation, as long as it is a hydrogen atom, halogen atom, hydrocarbon group or fluorine-containing alkyl group. Examples of the preferable substituent are fluorine, chlorine, bromine and the like as the halogen atom; methyl group, ethyl group, propyl group, isopropyl group, butyl group, isobutyl group, sec-butyl group, tert-butyl group, cyclopentyl group, cyclohexyl group, phenyl group, benzyl group, phenethyl group and the like as the hydrocarbon group; and fluorine-containing alkyl groups in which hydrogen atoms of the alkyl group have partially or entirely been replaced with halogen atoms. In the case of the hydrocarbon group and the fluorine-containing alkyl group, however, the number of carbons is preferably about 1-20.

Furthermore, from the viewpoint of polymerizability, the number of carbons of 1-4 is preferably used. In particular, as the fluorine-containing alkyl group is exemplified, they are trifluoromethyl group of —$CF_3$, trifluoroethyl group of —$CH_2CF_3$, 1,1,1,3,3,3-hexafluoroisopropyl group and the like. They can be used without their structural limitation. Examples of particularly preferable structures can be monomers that are specifically shown as the following general formulas (2) to (5).

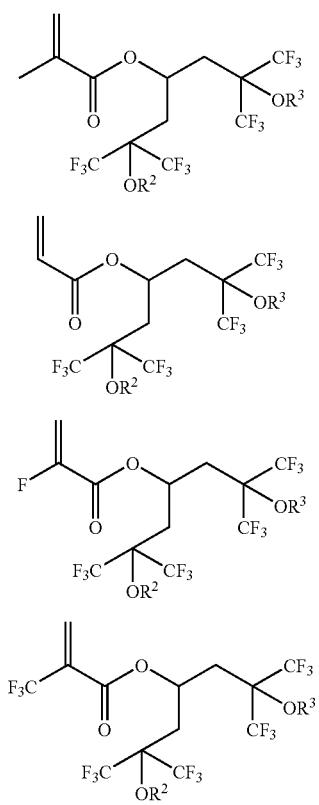

$R^2$ and $R^3$ usable herein are hydrogen atoms, fluorine atoms, hydrocarbon groups optionally branched, fluorine-containing alkyl groups, aromatic groups, or cyclic structures containing an aliphatic group and may contain oxygen or carbonyl bond. The structure is not particularly limited. Hydroxyl group (each of $R^2$ and $R^3$ is a hydrogen atom), which is the simplest and has high transparency, is fundamental. Thereover, depending on the intended purpose, it can be protected or modified with hydrocarbon groups of about 1-20 carbons, optionally having a cyclic structure, such as methyl group, ethyl group, isopropyl group, cyclopropyl group, cyclopentyl group, cyclohexyl group, nornornel group, adamantyl group and benzyl group; chain ether groups, such as methoxy methyl ether and methoxyethoxy methyl ether, as ones containing oxygen atom; 4-methoxybenzyl group as aromatics; and acetyl group, pivaloyl group, tert-butoxycarbonyl group, benzoyl group and the like, as ones containing carbonyl group. Its purpose is to provide characteristics such as dissolution in organic solvents and alkali aqueous solutions, high glass transition point, crosslinkability for purposes of solder heat resistance, positive-type photosensitivity due to photoacid generator, and etching resistance. It is possible to use a different one in each applied field of the present invention. $R^2$ and $R^3$ may be identical or different.

In the following, the process for synthesizing the α, β-unsaturated ester represented by the general formula (1) is described. According to the present invention, the synthesis process is not particularly limited. It suffices that the monomer of the general formula (1) is finally produced. The following processes can be cited as examples of the typical synthesis examples.

That is, the α, β-unsaturated ester represented by the general formula (1) is synthesized by a condensation between an alcohol derived from hexafluoroacetone and acetone (see Loeb, Stephen J., Martin, John W. L., et al, Canadian Journal of Chemistry, 56, 2369(1978)) and an α, β-unsaturated carboxylic acid such as acrylic acid, methacrylic acid and 2-trifluoromethylacrylic acid.

As exemplified in more detail, it can be synthesized by a general process, such as a condensation reaction with an α, β-unsaturated carboxylic halide, such as acrylic chloride, methacrylic chloride, 2-fluoroacrylic acid and 2-trifluoromethylacrylic chloride, under a basic condition such as an alkali metal hydride or amine compound, or a dehydration and condensation reaction with an α, β-unsaturated carboxylic acid, such as acrylic acid, methacrylic acid, 2-fluoroacrylic acid and 2-trifluoromethylacrylic acid, in the presence of sulfuric acid, hydrochloric acid, methanesulfonic acid, trifluoromethanesulfonic acid and various Lewis acids.

The separation and purification of the product after each reaction may be conducted by a conventional process. For example, it is possible to use concentration, distillation, extraction, recrystallization, filtration, column chromatography and the like. It is optional to combine processes of at least two kinds.

Next, the polymer compound according to the present invention is described. According to the present invention, it is possible to use homopolymerization of the polymerizable monomer represented by the general formula (1), or copolymers formed of a plurality of combinations of the general formula (1), and copolymers with polymerizable other monomers.

As specific examples of the monomer copolymerizable with the monomer represented by the general formula (1) of the present invention, there is preferable at least one monomer selected from olefins, fluorine-containing olefins, acrylic esters, methacrylic esters, fluorine-containing acrylic esters, fluorine-containing methacrylic esters, norbornene compounds, fluorine-containing norbornene compounds, styrene compounds, fluorine-containing styrene compounds, vinyl ethers, and fluorine-containing vinyl ethers.

The olefin can be exemplified by ethylene and propylene. The fluoroolefin can be exemplified by vinyl fluoride, vinylidene fluoride, trifluoroethylene, chlorotrifluoroethylene, tetrafluoroethylene, hexafluoropropylene, and hexafluoroisobutene.

Acrylic esters or methacrylic esters that are usable in the present invention can be used without particular limitation with respect to ester side chains. As known compounds are specified, it is possible to use alkyl esters of acrylic acid or methacrylic acid, such as methyl acrylate or methacrylate, ethyl acrylate or methacrylate, n-propyl acrylate or methacrylate, isopropyl acrylate or methacrylate, n-butyl acrylate or methacrylate, isobutyl acrylate or methacrylate, n-hexyl acrylate or methacrylate, n-octyl acrylate or methacrylate, 2-ethylhexyl acrylate or methacrylate, lauryl acrylate or methacrylate, 2-hydroxyethyl acrylate or methacrylate, and 2-hydroxypropyl acrylate or methacrylate; acrylates or methacrylates containing ethylene glycol, propylene glycol and tetramethylene glycol; unsaturated amides such as acrylic amide, methacrylic amide, N-methylolacrylic amide, N-methylolmethacrylic amide and diacetoneacrylic amide; acrylonitrile, methacrylonitrile, alkoxysilane-containing vinyl silanes, acrylic or methacrylic esters, tert-butyl acrylate or methacrylate, 3-oxocyclohexyl acrylate or methacrylate, adamantyl acrylate or methacrylate, alkyladamantyl acrylate or methacrylate, cyclohexyl acrylate or methacrylate, tricyclodecanyl acrylate or methacrylate, acrylates or methacrylates having cyclic structures such as lactone ring and norbornene ring, acrylic acid, methacrylic acid, and the like. Furthermore, it is also possible to copolymerize maleic acid, fumaric acid, maleic anhydride and the like as the above acrylate compounds containing an α-cyano group and analogous compounds.

The fluorine-containing acrylic ester or fluorine-containing methacrylic ester may be an acrylic ester or methacrylic ester having a fluorine atom-containing group at the acrylic α-position or ester moiety. A cyano group may be introduced into α-position. For example, as a monomer in which a fluorine-containing alkyl group has been introduced into α-position, there is preferably used a monomer in which the above-mentioned non-fluoric acrylic ester or methacrylic ester has been provided at α-position with trifluoromethyl group, trifluoroethyl group, or the like.

On the other hand, it is an acrylic ester or methacrylic ester having a unit in which a fluorine-containing alkyl group that is a perfluoroalkyl group or fluoroalkyl group is contained as ester moiety or in which a cyclic structure and fluorine atom are coexistent in ester moiety. The cyclic structure is, for example, a fluorine-containing benzene ring, fluorine-containing cyclopentane ring, fluorine-containing cyclohexane ring, fluorine-containing cycloheptane ring or the like, in which a fluorine atom or trifluoromethyl group has been substituted. It is possible to use an acrylic or methacrylic ester having an ester moiety that is a fluorine-containing t-butyl ester group. Of such units, as particularly representative ones are exemplified in the form of monomer, there are cited 2,2,2-trifluoroethylacrylate, 2,2,3,3-tetrafluoropropylacrylate, 1,1,1,3,3,3-hexafluoroisopropylacrylate, heptafluoroisopropylacrylate, 1,1-dihydroheptafluoro-n-butylacrylate, 1,1,5-trihydrooctafluoro-n-pentylacrylate, 1,1,2,2-tetrahydrotridecafluoro-n-octylacrylate, 1,1,2,2-tetrahydroheptadecafluoro-n-decylacrylate, 2,2,2-trifluoroethylmethacrylate, 2,2,3,3-tetrafluoropropylmethacrylate, 1,1,1,3,3,3-hexafluoroisopropylmethacrylate, heptafluoroisopropylmethacrylate, 1,1-dihydroheptafluoro-n-butylmethacrylate, 1,1,5-trihydrooctafluoro-n-pentylmethacrylate, 1,1,2,2-tetrahydrotridecafluoro-n-octylmethacrylate, 1,1,2,2-tetrahydroheptadecafluoro-n-decylmethacrylate, perfluorocyclohexylmethylacrylate, perfluorocyclohexylmethylmethacrylate, and the like.

It is possible to use styrene compounds, fluorine-containing styrene compounds, vinyl ethers, fluorine-containing vinyl ethers, allyl ethers, vinyl esters, vinyl silanes, and the like. Herein, as the styrene compounds and the fluorine-containing styrene compounds, it is possible to use a styrene compound, in which hexafluoroacetone has been added, a styrene or hydroxystyrene containing trifluoromethyl group substituted for hydrogen, and the above styrene or fluorine-containing styrene compound having a halogen, alkyl group or fluorine-containing alkyl group bonded to α-position, as well as styrene, fluorinated styrene, hydroxystyrene and the like.

Vinyl ethers, fluorine-containing vinyl ethers, allyl ethers, vinyl esters and the like are generally said to be inferior in polymerizability with the monomer of the general formula (1) according to the present invention. It is, however, possible to introduce them depending on their copolymerization ratio. For example, they are alkyl vinyl ethers optionally containing methyl group, ethyl group, or hydroxyl group such as hydroxyethyl group or hydroxybutyl group. Their hydrogen may be partially or entirely replaced with fluorine. It is also possible to use cyclohexyl vinyl ether, cyclic vinyl ethers containing a hydrogen or carbonyl bond in their cyclic structure, and monomers in which hydrogen of those cyclic vinyl ethers has been partially or entirely replaced with fluorine. Furthermore, it is possible to use allyl ethers, vinyl esters vinyl silanes without particular limitation as long as they are known compounds.

Furthermore, the norbornene compounds and the fluorine-containing norbornene compounds are norbornene monomers having a mononucleus or multinucleus structure. These are capable of copolymerizing with the monomer of the general formula (1). They are generally said to be inferior in copolymerizability with acrylic ester compounds such as the general formulas (2) and (3). It is, however, possible to achieve a copolymerization with a monomer represented by the general formula (2) or (3), depending on the combination of the copolymerization of the third component and subsequent ones. Upon this, as the norbornene compound, it is preferable to use a norbornene compound obtained by conducting a Diels-Alder addition reaction of an unsaturated compound, such as allyl alcohol, fluorine-containing allyl alcohol, acrylic acid, 2-fluoroacrylic acid, methacrylic acid, all of the acrylic esters or methacrylic esters described in the present specification and fluorine-containing acrylic esters or methacrylic esters, and cyclopentadiene or cyclohexadiene.

These polymerizable compounds may be used alone or may be used in combination of at least two kinds. According to the present invention, the copolymerization compositional ratio of the monomer of the general formula (1) is used without particular limitation. The selection is preferably between 10-100%, more preferably 30-100%. If it is less than 30%, it is not possible to achieve sufficient transparency and film forming property depending on the wavelength range of the applied field.

The polymerization process of the polymer compound according to the present invention is not particularly limited, as long as it is a process generally used. Radical polymerization, ionic polymerization and the like are preferable. In some cases, it is also possible to use coordinated anionic polymerization, living anionic polymerization, and the like. Herein, we describe radical polymerization, which is more general.

That is, it may be conducted by a known polymerization process such as bulk polymerization, solution polymerization, suspension polymerization or emulsion polymerization, in the presence of a radical polymerization initiator or radical initiating source, by a batch-wise, half-continuous or continuous operation.

The radical polymerization initiator is not particularly limited. As examples, azo compounds, peroxides and redox compounds are cited. In particular, azobisisobutyronitrile, t-butylperoxypivalate, benzoyl peroxide, and the like are preferable.

The reaction vessel used in the polymerization is not particularly limited. In the polymerization, it is optional to use a polymerization solvent. As the polymerization solvent, one that does not interfere with the radical polymerization is preferable. Its representative ones are esters such as ethyl acetate and n-butyl acetate; ketones such as acetone, methyl ethyl ketone and methyl isobutyl ketone; hydrocarbons such as toluene and cyclohexane; and alcohol solvents such as isopropyl alcohol and ethylene glycol monomethyl ether.

Furthermore, it is also possible to use various solvents such as water, ethers, cyclic ethers, fluorohydrocarbons, and aromatics. These solvents can be used singly or in a mixture of at least two kinds. Furthermore, it is possible to use a molecular weight adjusting agent such as mercaptan. The reaction temperature of the copolymerization is suitably changed depending on the radical polymerization initiator or radical polymerization initiating source. It is generally preferably 20-200° C., particularly preferably 30-140° C.

As a process of removing an organic solvent or water as the medium from the thus obtained solution or dispersion of the polymer compound according to the present invention, any known process can be used. For example, it is a process such as reprecipitation filtration or heated distillation under reduced pressure.

The present invention provides a fluorine-containing acrylate compound that is a functional monomer having water repellency, oil repellency, low water absorption, heat resistance, weather resistance, corrosion resistance, transparency, photosensitivity and the like, by making it have high fluorine content and polar groups in the same molecule, and that is a novel polymerizable monomer having high transparency in a wide wavelength range, that is, from vacuum ultraviolet ray to optical communication wavelength range and having adhesion to substrate and high film forming property, and a polymer compound using the same.

It is possible to use the polymer compound of the present invention as a photoresist material by dissolving it in an organic solvent or water and by adding acid generator or other additives by a known method. In particular, since it is a polymer compound of high fluorine content, it shows high transparency in a short wavelength range such as 193 nm (ArF laser) and 157 nm ($F_2$ laser). Therefore, it is suitable for a resist material, to which transparency in vacuum ultraviolet wavelength range has been applied, and becomes a material suitable for producing electronic devices such as semiconductor.

Next, the present invention is described in more detail by examples. In the following, synthesis examples of the polymerizable monomers of the present invention are shown in 1-3. Furthermore, polymer synthesis examples are shown in Synthesis Examples 4-9.

Synthesis Example 1

Synthesis of an Alcohol Represented by the Following Formula (7)

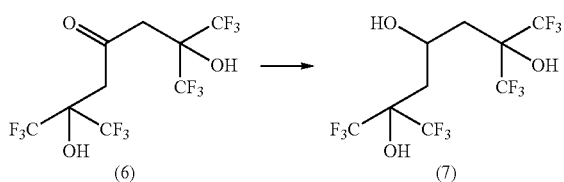

Sodium borohydride (6.30 g, 166.6 mmol) was added little by little under cooling with ice by spending 11 min to an ethanol (256 ml) solution of 1,1,1,7,7,7-hexafluoro-2,6-dihydroxy-2,6-bis(trifluoromethyl)-4-heptanone of the formula (6) (50.00 g, 128.1 mmol). Under nitrogen atmosphere, stirring was conducted under cooling with ice for 30 min. By an analysis of the reaction liquid by gas chromatography, conversion of the ketone was 100%, and the formation of the formula (7) was found.

2N hydrochloric acid was added little by little under cooling with ice to the reaction liquid to hydrolyze the same, followed by extraction of the organic matter with diethyl ether. Then, the organic layer was washed with pure water and saturated brine, followed by drying with magnesium sulfate anhydride. Then, the solvent was removed by evaporator, thereby obtaining a crude product (47.71 g) of the formula (7) as white crystals.

Synthesis Example 2

Synthesis of a Methacrylate Represented by the Formula (8)

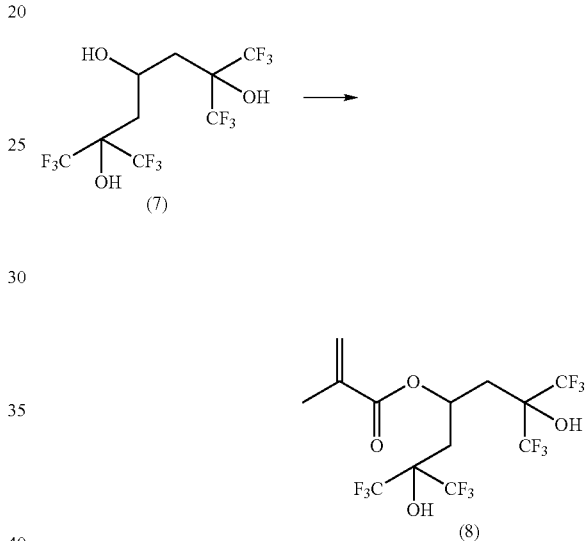

2,2'-methylene-bis(4-methyl-6-t-butylphenol) (50 mg) was added as a polymerization inhibitor to a methacrylic acid (4.41 g, 51.20 mmol) solution of the crude product (10.04 g, 25.60 mmol) of the formula (7). Then, concentrated sulfuric acid (5.02 g, 51.20 mmol) was added dropwise at room temperature, followed by stirring at 80° C. for 4 hr. By an analysis of the reaction liquid by gas chromatography, conversion to the formula (8) was 76.5%, and the raw material alcohol (7) was in 17.7%.

The reaction liquid was poured into iced water, followed by extraction of the organic matter with diethyl ether. Then, the organic layer was washed with saturated sodium hydrogencarbonate aqueous solution, pure water and saturated brine, followed by drying with magnesium sulfate anhydride. Then, the solvent was removed by evaporator, followed by single distillation to obtain the formula (8) (90-91.5 mmHg/1 mmHg, 4.76 g, 10.34 mmol; purity: 94.4 GC %) as a colorless, transparent liquid.

The spectrum data of the formula (8) are as follows.

$^1$H-NMR(CDCl$_3$, TMS standard) δ: 6.21 (1H, br-s), 5.76 (1H, br-s), 5.44-5.38 (1H, m), 4.85 (2H, s), 2.45 (2H, dd, J=16.0, 6.0 Hz), 2.37 (2H, dd, J=16.0, 4.0 Hz), 1.96 (3H, s)

$^{19}$F-NMR(CDCl$_3$, CFCl$_3$ standard) δ: −77.2 (6F, q, J=9.0 Hz), −78.9 (6F, q, J=9.0 Hz)

Synthesis Example 3

Synthesis of 2-trifluoromethylacrylate Represented by the Following Formula (9)

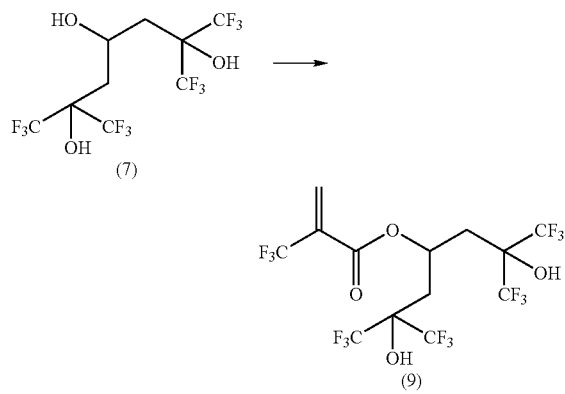

Concentrated sulfuric acid (0.50 g, 5.10 mmol) was added dropwise at room temperature to a mixture of the crude product (1.00 g, 2.55 mmol) of the formula (7) and 2-trifluoromethylacrylic acid (0.71 g, 5.10 mmol), followed by stirring at 80° C. for 2 hr. By an analysis of the reaction liquid by gas chromatography, conversion to the formula (9) was 82.0%, and the raw material alcohol (7) was in 13.1%.

The reaction liquid was poured into iced water, followed by extraction of the organic matter with diethyl ether. Then, the organic layer was washed with saturated sodium hydrogencarbonate aqueous solution, pure water and saturated brine, followed by drying with magnesium sulfate anhydride. Then, the solvent was removed by evaporator, followed by a separation purification by silica gel column chromatography to obtain the formula (9) (0.82 g, 1.59 mmol, purity: 92.3 GC %) as a colorless, transparent liquid.

Synthesis Example 4

Synthesis of a Homopolymer of a Methacrylic Ester Represented by the Following Formula (10)

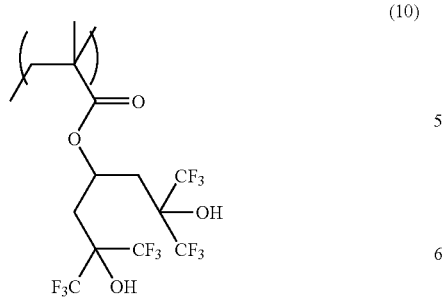

Under nitrogen atmosphere, AIBN (1.4 mg, 2 mol %) was added at room temperature to a methyl ethyl ketone (198.1 mg) solution of the formula (8) (198.1 mg), followed by immersion in an oil bath of 65° C. and stirring for 17 hr. This polymerization liquid was reprecipitated in n-hexane (11.9 g) at room temperature. Then, the polymer was filtered and recovered. The obtained polymer was dried under reduced pressure in a 60° C. oven for 3 hr, thereby obtaining a white-color powder of a homopolymer (183.9 mg, yield: 92.8%) represented by the formula (10). The molecular weight was Mn/Mw=37,700/82,300 by polystyrene conversion. AIBN represents azobisisobutyronitrile, which is a polymerization initiator.

Synthesis Example 5

Synthesis of a Copolymer Represented by the Following Formula (11)

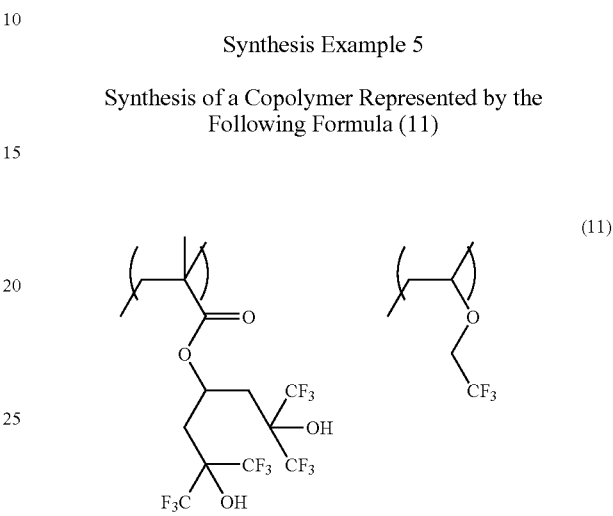

Under nitrogen atmosphere, AIBN (1.4 mg, 2 mol %) was added at room temperature to a methyl ethyl ketone (124.3 mg) solution of the formula (8) (97.6 mg, 0.21 mmol) and 2,2,2-trifluoroethyl vinyl ether (26.7 mg, 0.21 mmol), followed by immersion in an oil bath of 65° C. and stirring for 17 hr. This polymerization liquid was reprecipitated in n-hexane (7.4 g) at room temperature. Then, the polymer was filtered and recovered. The obtained polymer was dried under reduced pressure in a 60° C. oven for 3 hr, thereby obtaining a pale-yellow color powder of a copolymer (83.7 mg, yield: 68.4%) represented by the formula (11). The molecular weight was Mn/Mw=36,800/81,000 by polystyrene conversion. The composition ratio was methacrylic ester/vinyl ether=86.2/13.8 by $^{19}$F-NMR.

Synthesis Example 6

Synthesis of a Copolymer Represented by the Following Formula (12)

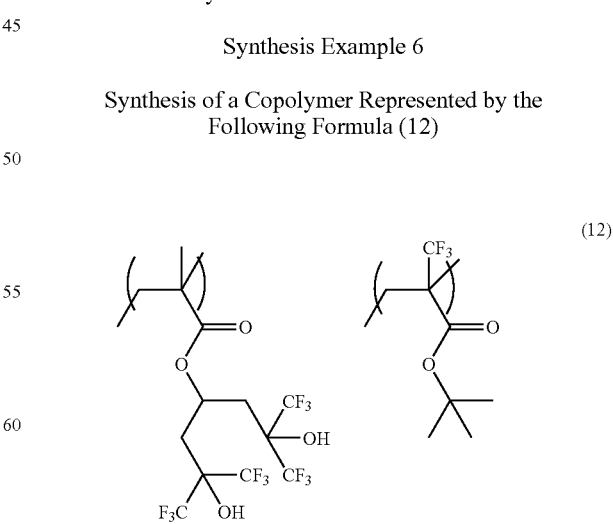

Under nitrogen atmosphere, AIBN (1.4 mg, 2 mol %) was added at room temperature to a methyl ethyl ketone (139.1 mg) solution of the formula (8) (97.5 mg, 0.21 mmol) and t-butyl 2-trifluoromethylacrylic ester (41.6 mg, 0.21 mmol), followed by immersion in an oil bath of 65° C. and stirring for 17 hr. This polymerization liquid was reprecipitated in n-hexane (8.3 g) at room temperature. Then, the polymer was filtered and recovered. The obtained polymer was dried under reduced pressure in a 60° C. oven for 3 hr, thereby obtaining a white-color powder of a copolymer (70.1 mg, yield: 49.6%) represented by the formula (12). The molecular weight was Mn/Mw=18,500/54,600 by polystyrene conversion. The composition ratio was methacrylic ester/2-trifluoromethylacrylic ester=82.8/17.2 by $^{19}$F-NMR.

Synthesis Example 7

Synthesis of a Copolymer Represented by the Following Formula (13)

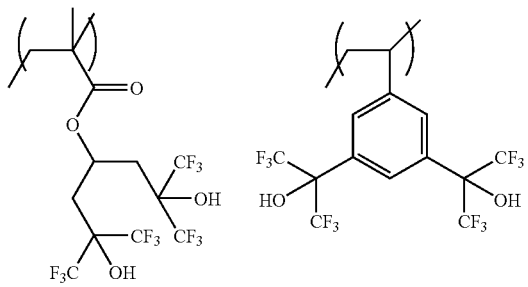

(13)

Under nitrogen atmosphere, AIBN (1.4 mg, 2 mol %) was added at room temperature to a methyl ethyl ketone (195.9 mg) solution of the formula (8) (100.4 mg, 0.22 mmol) and 3,5-bis(hexafluoroisopropyl alcohol)styrene (95.5 mg, 0.22 mmol), followed by immersion in an oil bath of 65° C. and stirring for 17 hr. This polymerization liquid was reprecipitated in n-hexane (11.7 g) at room temperature. Then, the polymer was filtered and recovered. The obtained polymer was dried under reduced pressure in a 60° C. oven for 3 hr, thereby obtaining a white-color powder of a copolymer (180.9 mg, yield: 91.7%) represented by the formula (13). The molecular weight was Mn/Mw=28,900/113,800 by polystyrene conversion. The composition ratio was methacrylic ester/styrene=48.0/52.0 by $^{19}$F-NMR. AIBN represents azobisisobutyronitrile, which is a polymerization initiator.

Synthesis Example 8

Synthesis of a Terpolymer Represented by the Following Formula (14)

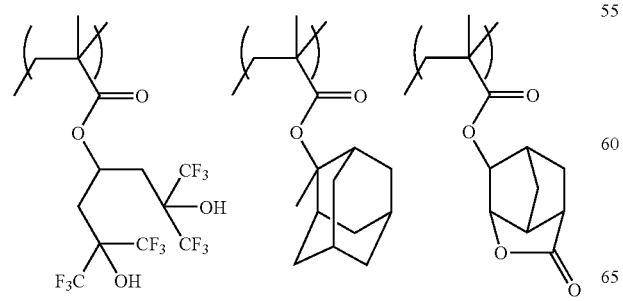

(14)

Under nitrogen atmosphere, AIBN (2.1 mg, 2 mol %) was added at room temperature to a methyl ethyl ketone (197.2 mg) solution of the formula (8) (99.0 mg, 0.21 mmol), 2-(2-methyladamantyl)methacrylate (50.4 mg, 0.21 mmol) and 5-(3-oxatricyclo[4.2.1.0$^{4,8}$]nonan-2-one)methacrylate (47.8 mg, 0.21 mmol), followed by immersion in an oil bath of 65° C. and stirring for 17 hr. This polymerization liquid was reprecipitated in n-hexane (11.8 g) at room temperature. Then, the polymer was filtered and recovered. The obtained polymer was dried under reduced pressure in a 60° C. oven for 3 hr, thereby obtaining a white-color powder of a terpolymer (180.3 mg, yield: 89.9%) represented by the formula (14). The molecular weight was Mn/Mw=23,600/97,000 by polystyrene conversion. The composition ratio was the formula (8)/adamantyl/lactone=28.4/31.3/40.3 by the weight reduction by TG-DTA and $^1$H-NMR.

Synthesis Example 9

Synthesis of a Copolymer Represented by the Following Formula (15)

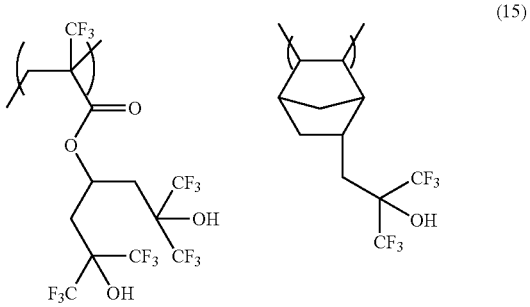

(15)

Under nitrogen atmosphere, AIBN (1.4 mg, 2 mol %) was added at room temperature to a methyl ethyl ketone (156.3 mg) solution of the formula (8) (98.7 mg, 0.21 mmol) and 3-(5-bicyclo[2.2.1]2-heptenyl-1,1,1-trifluoro-2-(trifluoromethyl)2-propanol (57.6 mg, 0.21 mmol), followed by immersion in an oil bath of 65° C. and stirring for 17 hr. This polymerization liquid was reprecipitated in n-hexane (9.4 g) at room temperature. Then, the polymer was filtered and recovered. The obtained polymer was dried under reduced pressure in a 60° C. oven for 3 hr, thereby obtaining a white-color powder of a copolymer (0.86 mg, yield: 55.1%) represented by the formula (15). The molecular weight was Mn/Mw=12,600/31,100 by polystyrene conversion. The composition ratio was 2-trifluoromethylacrylic ester/norbornene=60.8/39.2 by $^{19}$F-NMR.

The invention claimed is:

1. A polymerizable acrylate compound represented by the general formula (1):

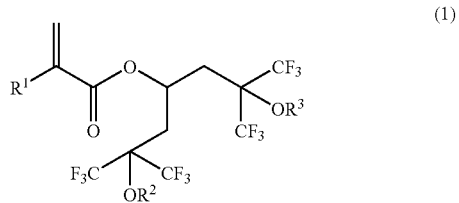

(1)

(in the formula, $R^1$ represents a hydrogen atom, halogen atom, hydrocarbon group or fluorine-containing alkyl group, $R^2$ and $R^3$ may be different or identical, and each of them independently is a hydrogen atom, fluorine atom, hydrocarbon group optionally branched, fluorine-containing alkyl group, aromatic group, or cyclic structure containing an aliphatic group and may contain oxygen or carbonyl bond).

2. A polymerizable acrylate compound according to claim 1, which is characterized in that each of the hydrocarbon group and the fluorine-containing alkyl group has a carbon number of 1-20.

3. A polymerizable acrylate compound according to claim 1, which is characterized in that each of the hydrocarbon group and the fluorine-containing alkyl group has a carbon number of 1-4.

4. A polymerizable acrylate compound according to claim 1, which is characterized by being represented by any one of the general formulas (2) to (5),

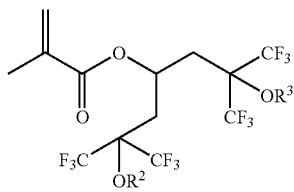
(2)

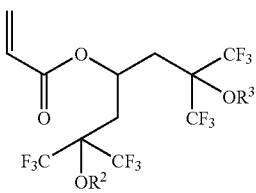
(3)

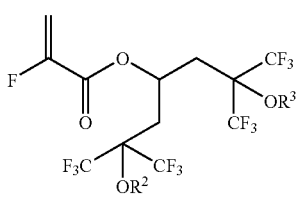
(4)

-continued

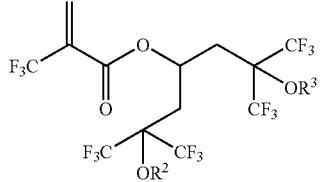
(5)

(in the formulas $R^2$ and $R^3$ are defined as in the general formula (1)).

5. A polymerizable acrylate compound according to claim 1, which is characterized in that each of $R^2$ and $R^3$ of the general formula (1) is a hydrogen atom.

6. A polymer compound obtained by a polymerization or copolymerization using a polymerizable acrylate compound according to claim 1.

7. A polymer compound according to claim 6, which is characterized by being obtained by a copolymerization with at least one monomer selected from olefins, fluorine-containing olefins, acrylic esters, methacrylic esters, fluorine-containing acrylic esters, fluorine-containing methacrylic esters, norbornene compounds, fluorine-containing norbornene compounds, styrene compounds, fluorine-containing styrene compounds, vinyl ethers, and fluorine-containing vinyl ethers.

8. A polymer compound according to claim 6, which is characterized by containing a unit represented by the following formula (10)

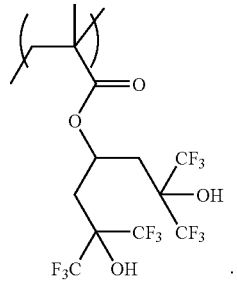
(10)

9. A polymer compound according to claim 6, which is characterized by containing two units represented by the following formula (11)

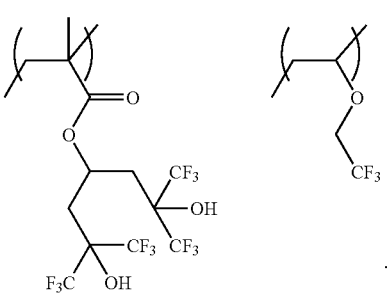
(11)

10. A polymer compound according to claim 6, which is characterized by containing two units represented by the following formula (12)

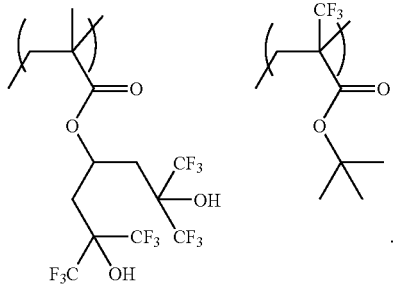

(12)

11. A polymer compound according to claim 6, which is characterized by containing two units represented by the following formula (13)

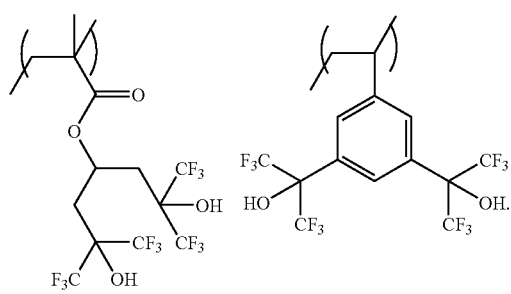

(13)

12. A polymer compound according to claim 6, which is characterized by containing three units represented by the following formula (14)

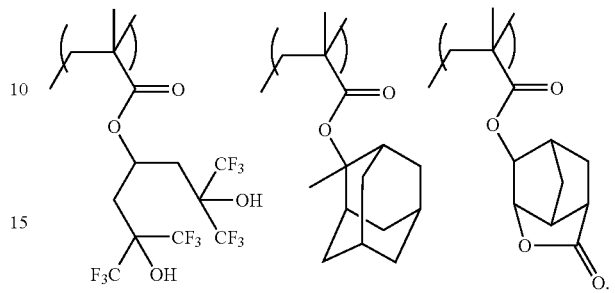

(14)

13. A polymer compound according to claim 6, which is characterized by containing two units represented by the following formula (15)

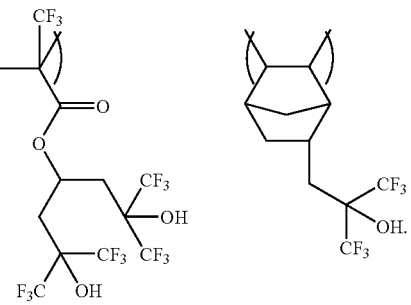

(15)

* * * * *